US012629261B1

(12) United States Patent
Yang et al.

(10) Patent No.: US 12,629,261 B1
(45) Date of Patent: May 19, 2026

(54) IMPLANT

(71) Applicant: INDUSTRIAL TECHNOLOGY RESEARCH INSTITUTE, Hsinchu (TW)

(72) Inventors: Kuo-Yi Yang, Hsinchu City (TW); Pei-I Tsai, Hsinchu City (TW); Kuo-Kuei Huang, Hsinchu County (TW); Shin-I Huang, Hsinchu City (TW); Shu-Fen Yeh, New Taipei City (TW); Shih-Ping Lin, Kaohsiung City (TW); Den-Tai Lin, Hsinchu City (TW); Wei-Lun Fan, Miaoli County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 19/004,491

(22) Filed: Dec. 30, 2024

(30) Foreign Application Priority Data

Dec. 26, 2024  (TW) .................................. 113150957

(51) Int. Cl.
*A61F 2/44* (2006.01)
*A61F 2/30* (2006.01)

(52) U.S. Cl.
CPC ....... *A61F 2/44* (2013.01); *A61F 2002/30011* (2013.01); *A61F 2002/30225* (2013.01);
(Continued)

(58) Field of Classification Search
CPC ............................................ A61F 2/44–2/447
See application file for complete search history.

(56) References Cited

U.S. PATENT DOCUMENTS 6,846,327 B2 *  1/2005  Khandkar ............. A61L 27/365
                                                    623/16.11
9,877,846 B2    1/2018  Dvorak et al.
(Continued)

FOREIGN PATENT DOCUMENTS

CN        102036613 B    10/2012
CN        102988122 A     3/2013
(Continued)

OTHER PUBLICATIONS

Mitchell I. Page et al., "Biomechanical evaluation of a novel repair strategy for intervertebral disc herniation in an ovine lumbar spine model," Frontiers in Bioengineering and Biotechnology, Oct. 25, 2022, 15 pages.
(Continued)

*Primary Examiner* — Julianna N Harvey
(74) *Attorney, Agent, or Firm* — CKC & Partners Co., LLC

(57) ABSTRACT

An implant is provided, and the implant includes a body, a limiting portion and a filling portion. The body has a first end portion, a second end portion opposite to the first end portion, and a middle portion disposed between the first end portion and the second end portion. The limiting portion includes a first solid structure and is located at the first end portion. The filling part includes an elastic structure and is located from the middle portion to the second end portion. A diameter of the first end portion of the body is greater than a diameter of the middle portion, and a diameter of the second end portion is greater than the diameter of the middle portion.

18 Claims, 14 Drawing Sheets

1

(52) U.S. Cl.

CPC .............. *A61F 2002/30327* (2013.01); *A61F 2002/30477* (2013.01); *A61F 2002/4435* (2013.01)

(56) References Cited

U.S. PATENT DOCUMENTS

| | | | |
|---|---|---|---|
| 10,046,084 | B2 | 8/2018 | Altschuler et al. |
| 10,799,361 | B2 | 10/2020 | Hauser et al. |
| 2003/0074075 | A1* | 4/2003 | Thomas, Jr. ........... A61B 17/70 623/908 |
| 2003/0078579 | A1 | 4/2003 | Ferree |
| 2003/0149483 | A1 | 8/2003 | Michelson |
| 2004/0039392 | A1 | 2/2004 | Trieu |
| 2007/0162131 | A1* | 7/2007 | Friedman ................ A61F 2/442 623/17.11 |
| 2008/0065218 | A1* | 3/2008 | O'Neil .................... A61F 2/442 623/17.16 |
| 2008/0140108 | A1 | 6/2008 | Matsuura et al. |
| 2008/0208344 | A1 | 8/2008 | Kilpela et al. |
| 2011/0029016 | A1 | 2/2011 | Yeung et al. |
| 2011/0153022 | A1 | 6/2011 | Singhatat et al. |
| 2011/0282456 | A1 | 11/2011 | Shafrir et al. |
| 2012/0316654 | A1 | 12/2012 | Seifert et al. |
| 2013/0274882 | A1 | 10/2013 | Guizzardi et al. |
| 2015/0305884 | A1 | 10/2015 | VonGunten |
| 2017/0143505 | A1 | 5/2017 | O'Halloran et al. |
| 2021/0077266 | A1 | 3/2021 | Hibri et al. |
| 2022/0062007 | A1 | 3/2022 | Seifert et al. |
| 2023/0058045 | A1* | 2/2023 | Park ..................... A61L 31/086 |
| 2023/0210672 | A1 | 7/2023 | Nie et al. |
| 2024/0099854 | A1 | 3/2024 | Hibri et al. |

FOREIGN PATENT DOCUMENTS

| | | |
|---|---|---|
| CN | 216221881 U | 4/2022 |
| CN | 115364271 A | 11/2022 |
| CN | 219126894 U | 6/2023 |
| CN | 118236206 A | 6/2024 |
| JP | 6963859 B1 | 11/2021 |
| TW | 200924725 A | 6/2009 |
| TW | 200927062 A | 7/2009 |
| TW | 201720388 A | 6/2017 |
| WO | 2008045638 A2 | 4/2008 |
| WO | 2023059887 A1 | 4/2023 |

OTHER PUBLICATIONS

Yangbin Wang et al., "Annulus Fibrosus Repair for Lumbar Disc Herniation: A Meta-Analysis of Clinical Outcomes From Controlled Studies," Global Spine Journal, Jan. 2024, vol. 14(1), pp. 306-321.

Pierce Nunley et al., "Lumbar Discectomy With Bone-Anchored Annular Closure Device in Patients With Large Annular Defects: One-Year Results," Cureus, Jun. 9, 2023, 11 pages.

Larry E Miller et al., "Expert review with meta-analysis of randomized and nonrandomized controlled studies of Barricaid annular closure in patients at high risk for lumbar disc reherniation," Expert Review Medical Devices, Apr. 1, 2020, 10 pages.

Kresten Rickers et al., "Biomechanical evaluation of annulus fibrosus repair with scaffold and soft anchors in an ex vivo porcine model," Sicot J., Sep. 7, 2018, 6 pages.

Dan Zhou et al., "Design principles in mechanically adaptable biomaterials for repairing annulus fibrosus rupture: A review," Bioactive Materials, in Jan. 2024, vol. 31, pp. 422-439.

Notice of Allowance of corresponding application TW113150957 issued on Jun. 19, 2025. (7 pages).

Extended European Search Report of corresponding application EP24223486.2 issued on May 27, 2025. (14 pages).

\* cited by examiner

IMPLANT

CROSS-REFERENCE TO RELATED APPLICATION

This application claims priority to Taiwan Application No. 113150957, filed Dec. 26, 2024, which is herein incorporated by reference in its entirety.

BACKGROUND

Field of Invention

The present disclosure relates to an implant. More particularly, the present disclosure relates to an implant for repairing an annulus fibrosus of an intervertebral disc.

Description of Related Art

Annulus fibrosus injury is a beginning of intervertebral disc problems and often directly leads to intervertebral disc pain. Repairing the annulus fibrosus is the key to treating intervertebral disc abnormalities. Since the intervertebral disc is lacking in blood circulation, the annulus fibrosus injury is difficult to self-healing. Current surgeries procedures are primarily fusion-based, which fixes a spine to reduce movement. However, the current surgeries cannot repair the annulus fibrosus and accelerates the degeneration of adjacent vertebrae. For herniated intervertebral disc, a surgery is often done to remove a protruding portion, but the surgery cannot completely cure the herniated intervertebral disc. Traditional implants are relatively rigid and prone to stress-shielding. If the implant is not securely fixed in the intervertebral disc, a bone plate adjacent to an implantation site may be damaged and bone erosion may occur, accelerating damage to the bone adjacent to the implantation site. In addition, poor fixation between the implant and surrounding tissues may be prone to cause secondary injury. Long-term improper posture or application of force by a patient suffering from the herniated intervertebral disc may exacerbate damage to the annulus fibrosus.

Therefore, there is an urgent need for a repair implant that can provide support to the intervertebral disc, minimize damage to the surrounding fibers, and be fixed to the intervertebral annulus fibrosus.

SUMMARY

Embodiments of this disclosure provide an implant for repairing an intervertebral annulus fibrosus. The implant includes a body, a limiting portion and a filling portion. The body having a first end portion, a second end portion, and a middle portion disposed between the first end portion and the second end portion. The limiting portion includes a first solid structure and is located at the first end portion. The filling portion includes an elastic structure and is located between the middle portion and the second end portion. A diameter of the first end portion of the body is greater than a diameter of the middle portion, and a diameter of the second end portion is greater than the diameter of the middle portion.

BRIEF DESCRIPTION OF THE DRAWINGS

In the following detailed description, for purposes of explanation, numerous specific details are set forth in order to provide a thorough understanding of the disclosed embodiments. It is to be noted that the drawings have been simplified to clearly illustrate the content of the embodiments, and the sizes of elements in the drawings are not drawn in the same proportion related to the actual products, so they are not used to limit the protected scope of the present disclosure. The accompanying drawings are described as follows.

DETAILED DESCRIPTION

In the following detailed description, for purposes of explanation, numerous specific details are set forth in order to provide a thorough understanding of the disclosed embodiments. According to the descriptions, claims and the drawings disclosed in the specification, a person skilled in the art may understand the concepts and features of the present disclosure. The following embodiments further illustrate various aspects of the present disclosure, but are not meant to limit the scope of the present disclosure.

Embodiments of the present disclosure provide an implant, and the implant includes a filling portion and a limiting portion connected to the filling portion. The diameters of both end portions of the implant are greater than a diameter of a middle portion of the implant. Additionally, in some embodiments, the filling portion and the limiting portion of the implant are integrally formed. In some embodiments, the implant can be manufactured by conventional processes or using additive manufacturing (AM) process technology. In some embodiments, a material of the implant includes, but is not limited to, metals powders, alloys powders, ceramics powders, and polymeric materials for biomedical applications, such as polyetheretherketone (PEEK).

The implant of the various embodiments disclosed herein can change the stiffness of the implant by forming different ratios of solid structure and elastic structure, or by creating different porosities in different areas of the implant. The implant provided by the embodiments of the present disclosure is described below based on the first to seventh embodiments in conjunction with FIGS. 1A to 9B.

First Embodiment

Figure 1A:
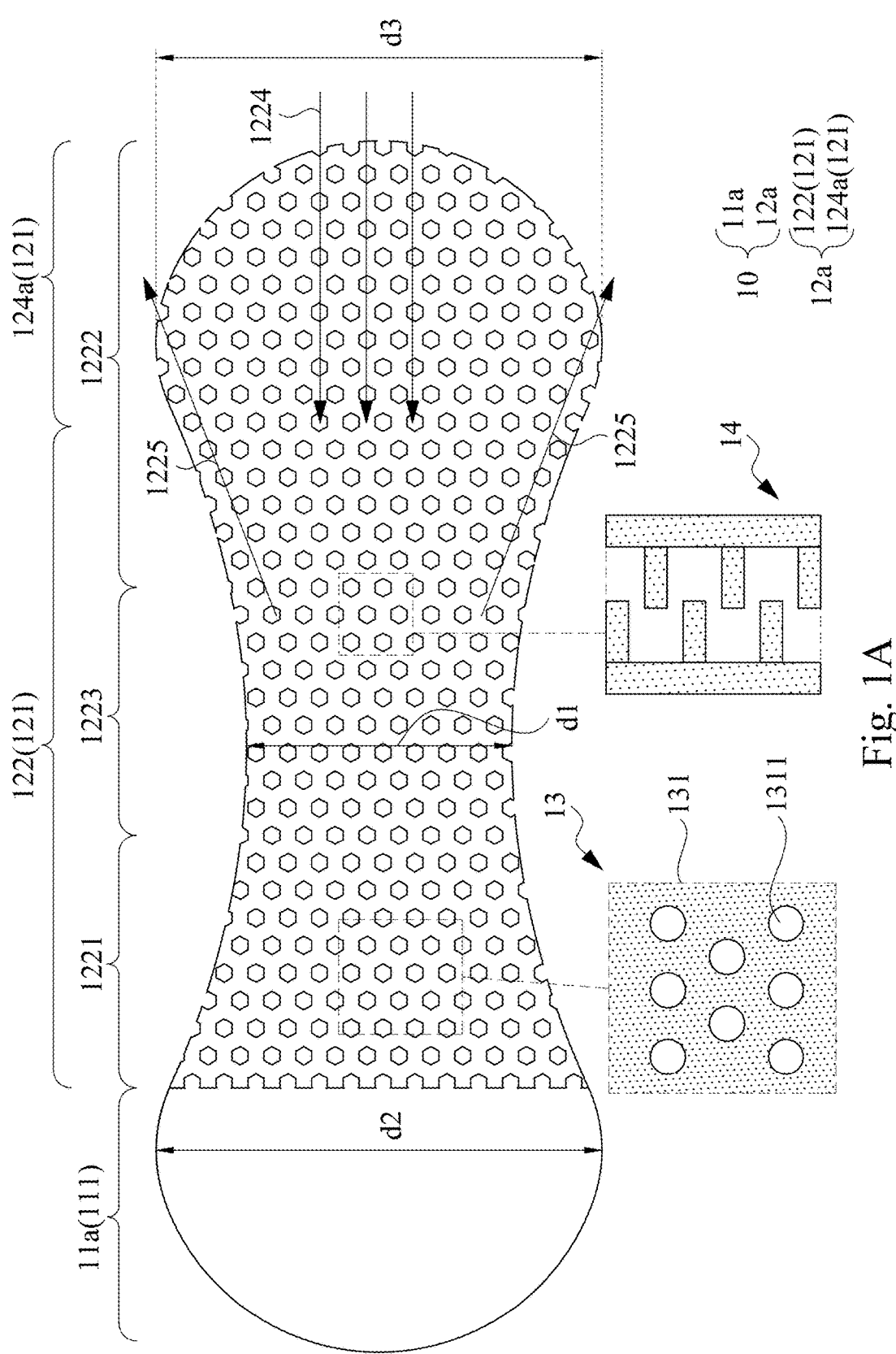
FIGS. 1A, 1B and 1C are schematic top views of an implant according to a first embodiment of the present disclosure, respectively.
Figure 1B:
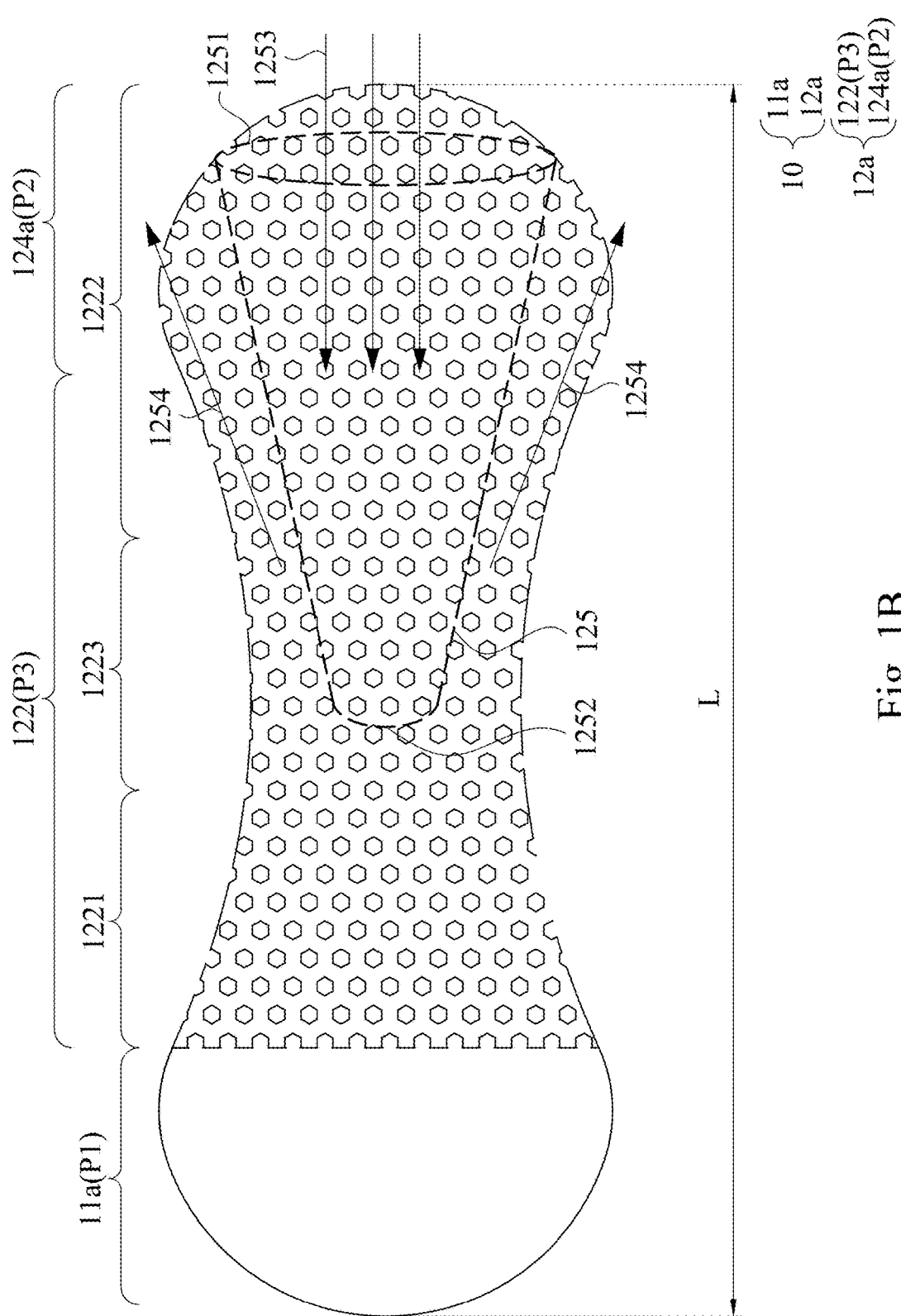
Figure 1C:
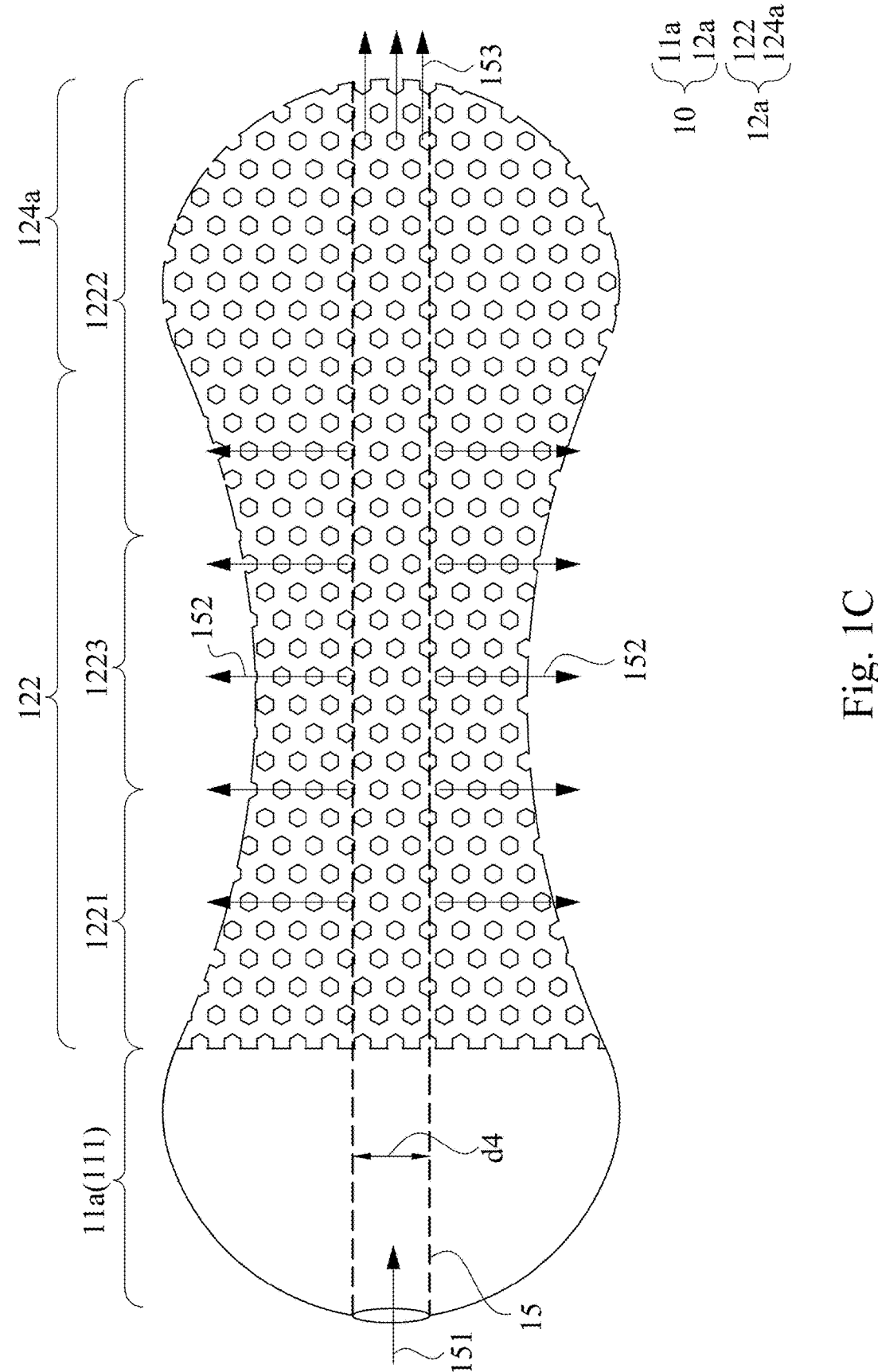

Please refer to FIGS. 1A and 1B. FIGS. 1A, 1B and 1C are schematic top views of an implant 1 according to a first embodiment of the present disclosure, respectively. The implant 1 includes a body 10, a limiting portion 11$a$ and a filling portion 12$a$. The body 10 is defined by a first end portion P1, a second end portion P2, and a middle portion P3 which is disposed between the first end portion P1 and the second end portion P2. The limiting portion 11$a$ is disposed at the first end portion P1 of the body 10 and includes a first solid structure 111. In this embodiment, the first solid structure 111 of the limiting portion 11$a$ is distributed at the first end portion P1 of the body 10. In addition, the limiting portion 11$a$ can secure the implant 1 in a cavity through a stiffness of the first solid structure 111, so that the implant 1 is fixed at a specific position in the cavity, preventing a liquid in the cavity from leaking. The filling portion 12$a$ is disposed from the middle portion P3 to the second end portion P2 of the body 10 and includes an elastic structure 121. In this embodiment, the elastic structure 121 of the filling portion 12$a$ is extended from the middle portion P3 to the second end portion P2 of the body 10. In some embodiments, a length L of the implant 1 is in a range of from 6 millimeters (mm) to 12 mm. In some embodiments, a ratio of the first solid structure 111 to the elastic structure 121 is in a range of from 1:1 to 1:8. The material stiffness of the implant 1 may be changed through adjusting the ratio of the first solid structure 111 to the elastic structure 121 of the implant 1.

In addition, a diameter of the first end portion P1 of the body 10 of the implant 1 is greater than a diameter of the middle portion P3 of the body 10 of the implant 1, and a diameter of the second end portion P2 of the body 10 of the implant 1 is greater than the diameter of the middle portion P3 of the body 10 of the implant 1. Specifically, the filling portion 12$a$ further includes a retracted portion 122 and an opening portion 124$a$. The retracted portion 122 has a first end and a second end opposite to the first end, the first end of the retracted portion 122 is connected to the limiting portion 11$a$, and the second end of the retracted portion 122 is connected to the opening portion 124$a$. The opening portion 124$a$ is disposed at the second end portion P2 of the body10, and the retracted portion 122 is disposed at the middle portion P3 of the body 10. The retracted portion 122 has a minimum diameter d1, and the minimum diameter d1 refers to a diameter of the narrowest section of the retracted portion 122. The limiting portion 11$a$ has a maximum diameter d2, and the maximum diameter d2 refers to a diameter of the widest porting of the limiting portion 11$a$. The opening portion 124$a$ has a maximum diameter d3, and the maximum diameter d3 refers to a diameter of the widest section of the opening portion 124$a$. The maximum diameter d2 is greater than the minimum diameter d1, and the maximum diameter d3 is greater than the minimum diameter d1. In some embodiments, the minimum diameter d1 is in a range from of 3 mm to 6 mm, and the maximum diameter d2 and the maximum diameter d3 are in ranges of from 6 mm to 9 mm, respectively.

The filling portion 12$a$ includes a plurality of pores (or holes), and the pores form a porous structure 13 in the filling portion 12$a$ of the implant 1. Although the pores in the first embodiment have different shapes and arrangements, a pore size of each of the pores is in a range from of 200 micrometers ($\mu$m) to 600 $\mu$m. The pore size is measured based on the widest width of each pore. Furthermore, in these embodiments, a porosity of the porous structure is in a range of from 20% to 80%.

In some embodiments, as shown in a dotted enlarged frame in FIG. 1A, the porous structure 13 includes a hole structure 131. That is, the hole structure 131 is formed by a plurality of pores 1311, and a shape of each pore 1311 includes a circle, a rectangle, a polygon or a combination thereof.

Figure 2B:
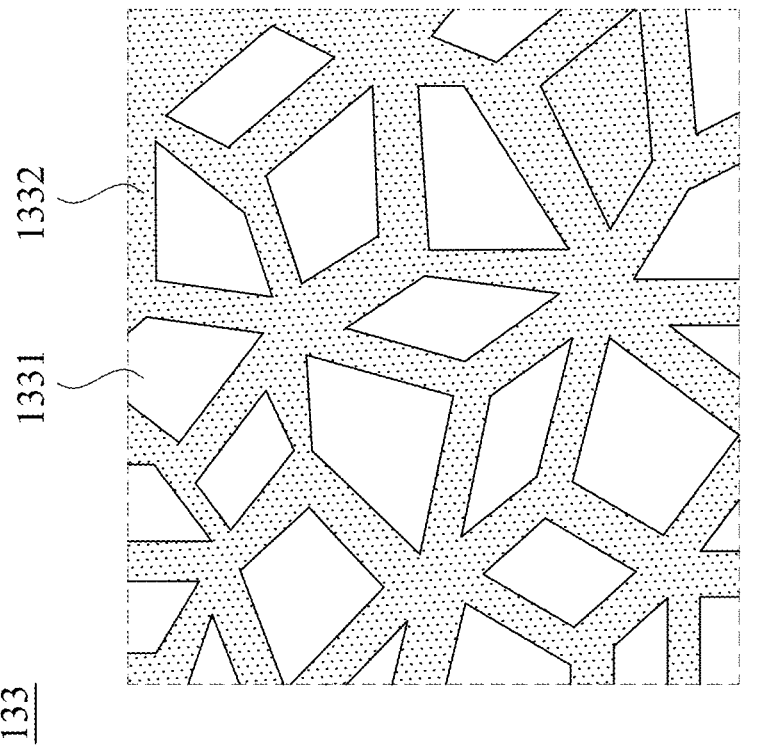
FIGS. 2A to 2B are schematic diagrams of a porous structure of an implant according to some embodiments of the present disclosure, respectively.
Figure 2A:
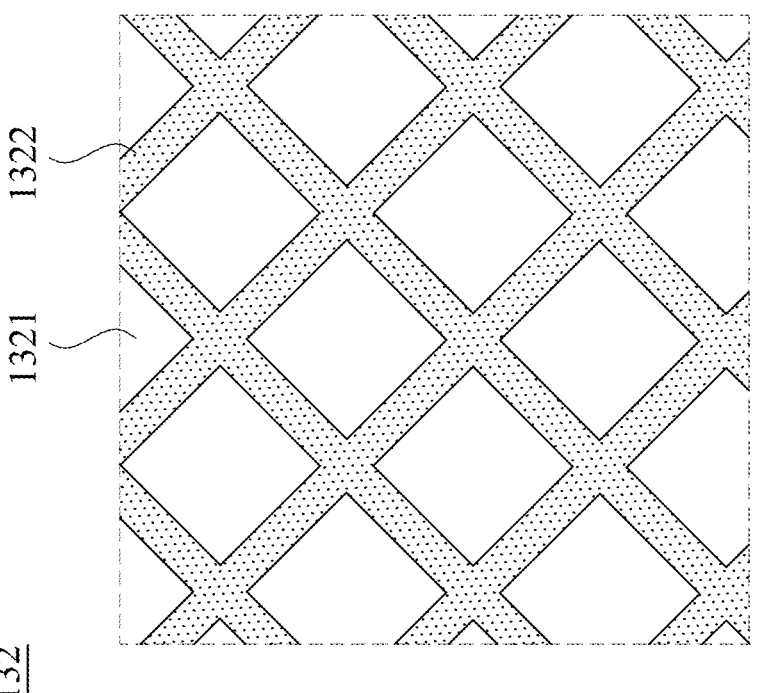

In some other embodiments, as shown in the schematic diagram of the porous structure in FIG. 2A, the porous structure 13 (such as shown in FIG. 1A) includes a regular grid structure 132. That is, the regular grid structure 132 is formed by stacking a plurality of linear materials 1322 to form a plurality of pores 1321. The linear materials 1322 include, but are not limited to, powder materials of metals powders, alloys powders, ceramics powders, and polymeric materials for biomedical applications. In the embodiment of FIG. 2A, a shape of each of the pores 1321 is a quadrilateral, such as a rhombus, but the shape of each of the pores 1321 may also be a parallelogram, a trapezoid, another polygon, or a combination thereof. Additionally, although in the embodiment of FIG. 2A, a pore size of each of the pores 1321 is illustrated to be substantially identical, the pore size of each of the pores 1321 may be different as long as the pores 1321 are regular shapes.

In some other embodiments, as shown in the schematic diagram of the porous structure in FIG. 2B, the porous structure 13 includes an irregular grid structure 133. That is, the irregular grid structure 133 is formed by stacking a plurality of linear materials 1332 to create a plurality of pores 1331. The linear materials 1332 include, but are not limited to, powder materials of metals powders, alloys powders, ceramics powders, and polymeric materials for biomedical applications. In the embodiment of FIG. 2B, a shape of each of the pores 1331 is an irregular quadrilateral, but the shape of each of the pores 1331 may also be an unequal-sided triangle, a polygon, a radial shape, or a combination thereof. In addition, in the embodiment of FIG. 2B, pore sizes of the pores 1331 are different. It can be understood that in some other embodiments, the porous structure 13 includes a hole structure 131 (as shown in FIG. 1A), a regular grid structure 132 (as shown in FIG. 2A), an irregular grid structure 133 or a combination thereof. In this embodiment, the pore sizes of the pores 1331 may be either substantially identical or different.

Please return to FIG. 1A. In some embodiments, the porous structure 13 is a gradient porous structure. The so-called "gradient porous structure" refers to that different pore sizes, densities, or porosities of the implant are arranged in different areas of the implant. For example, the pore sizes, the density, or the porosity of the implant varies from large to small, from small to large then to small, or from small to large. Further, a region of the filling portion 12$a$ proximal to the first end portion P1 is defined as a first region 1221, a region of the filling portion 12$a$ proximal to the second end portion P2 is defined as a second region 1222, and a region between the first region 1221 and the second region 1222 is defined as a third region 1223. The first region 1221 has a first porosity, the second region 1222 has a second porosity, and the third region 1223 has a third porosity. In some embodiments, the first porosity is less than the third porosity, and the third porosity is less than the second porosity. The porosity is greater, a fluid pressure is smaller, and relatively, the porosity is less, a smaller fluid pressure is greater. Therefore, in this embodiment, a reflow channel, as shown by arrows 1224 and 1225, can be formed in the implant 1 through the gradient porous structure. By means of a design of the reflow channel within the implant 1, a pressure in the cavity can be buffered, when the implant 1 is implanted in the cavity. Moreover, as shown by arrow 1224, when the liquid in cavity flows into the implant 1, a pressure is provided to the liquid flowing into the implant 1 through the first region 1221, the second region 1222 and the third region 1223 of the filling portion 12a in sequence. The liquid flowing into the implant 1 is then caused to flow back into the cavity, as shown by arrow 1225. As a result, in this embodiment, a first reflow path is formed through the reflow channel. In other words, the liquid flows back into the cavity due to the porosity differences among the different regions of the implant 1 after the liquid in the cavity flows into implant 1.

As shown in FIG. 1B, in some embodiments, the implant 1 includes a hollow structure 125, and the hollow structure 125 is disposed within the implant 1. The hollow structure 125 has a funnel-shaped and has a first end 1251 within the second region 1222 and a second end 1252 opposite to the first end 1251 and within the third region 1223. A radial dimension of the hollow structure 125 gradually expands toward the first end 1251, while the radial dimension of the hollow structure 125 gradually narrows toward the second end 1252. Although the hollow structure 125 in FIG. 1B is illustrated as being within the third region 1223 and extending to a portion of the second region 1222, the hollow structure 125 may also extend to the first region 1221. Of course, the shape of the hollow structure 125 is not limited. In this embodiment, in some embodiments, the first porosity is less than the third porosity, and the third porosity is less than the second porosity. The sizes of the pores of the first region 1221 are the smallest, as well as an opening of the second end 1252 of the hollow structure 125 is the smallest, so that an extrusion pressure of the liquid is the largest. In this manner, as shown by arrow 1253, when the liquid in the cavity flows into the implant 1 through the first end 1251 of the hollow structure 125, the liquid flowing into the implant 1 flows out of the second end 1252, and then the liquid is extruded back into the second region 1222 and the third region 1223 of the filling portion 12a. In addition, due to the presence of the hollow structure 125, the liquid flows back into the cavity from the filling portion 12a adjacent to an outer periphery of the hollow structure 125, as shown by arrow 1254. Consequently, another reflow channel may be formed within the implant 1 through the gradient porous structure, and the another reflow channel has a second reflow path. The second reflow path is that the liquid in the cavity flows into the implant 1 through the hollow structure 125, and then the liquid flows back into the cavity due to the porosity differences of the different regions of the implant 1. Moreover, since the second reflow path allows the liquid to flow into the implant 1 through the hollow structure 125, as shown by arrow 1253, and to flow out through the porous structure 13 (as shown in FIG. 1A), as shown by arrow 1254, the hollow structure 125 and the porous structure 13 may together form a buffer space within the implant 1 to help reduce the pressure in the cavity.

As shown in FIG. 1C, in some embodiments, the implant 1 includes a channel 15, and the channel 15 is disposed within the body 10 of the implant 1 and penetrates the body 10. For example, the channel 15 is disposed within the implant 1 along a central of the implant 1 for infusion of a fill factor substance, as shown by arrow 151. In some embodiments, the fill factor substance includes a growth factor substance that promotes cell or tissue growth, such as collagen or other growth factor-promoting substances, a bioglue that enhances a fixation of the implant 1, or a combination thereof. In some embodiments, a diameter d6 of the channel 15 is in a range of from 1 mm to 2 mm. In some embodiments, the diameter d6 of the channel 15 includes 0.35 mm, 0.45 mm, 0.55 mm, 0.65 mm, 0.75 mm, 0.85 mm, 0.95 mm, 1.05 mm, 1.15 mm, 1.25 mm, 1.35 mm, 1.45 mm, 1.55 mm, 1.65 mm, or any value between any two foregoing values. It is worth mentioning that, according to the requirements of the infused factor substance, the diameter d6 of the channel 15 can be designed to accommodate a needle with from 16G to 30G.

The infused factor substance is released into a cavity wall through the porous structure 13 of the filling portion 12a (as shown in FIG. 1A), as shown by arrow 152. Subsequently, the infused factor substance is released into the cavity, as shown by arrow 153. In some other embodiments, the implant 1 includes the channel 15, and the third porosity is greater than both the first porosity and the second porosity. In these embodiments, a reflow channel with a third reflow path may be formed in the implant 1 through the gradient porous structure, so as to inject the infused factor substance into the implant 1. For example, when the implant 1 is implanted into the cavity, the infused factor substance is allowed to remain in the middle portion P3 of the implant 1 by means of the design of the reflow channel within the implant 1. As well, the infused factor substance may be released through the plurality of pores to accelerate tissue regeneration at the implant site and/or enhance the fixation of the implant 1. Furthermore, due to a permeability of the porous structure 13, the infused factor substance does not flow back after entering the channel 15, while the infused factor substance is released into the cavity through the pores.

As shown in FIG. 1A, in some embodiments, the filling portion 12a includes a hollow structure 14 to increase the material stiffness of the filling portion 12a. In some embodiments, the filling portion 12a may include both the porous structure 13 and the hollow structure 14 to adjust the stiffness of the implant 1.

Figure 3A:
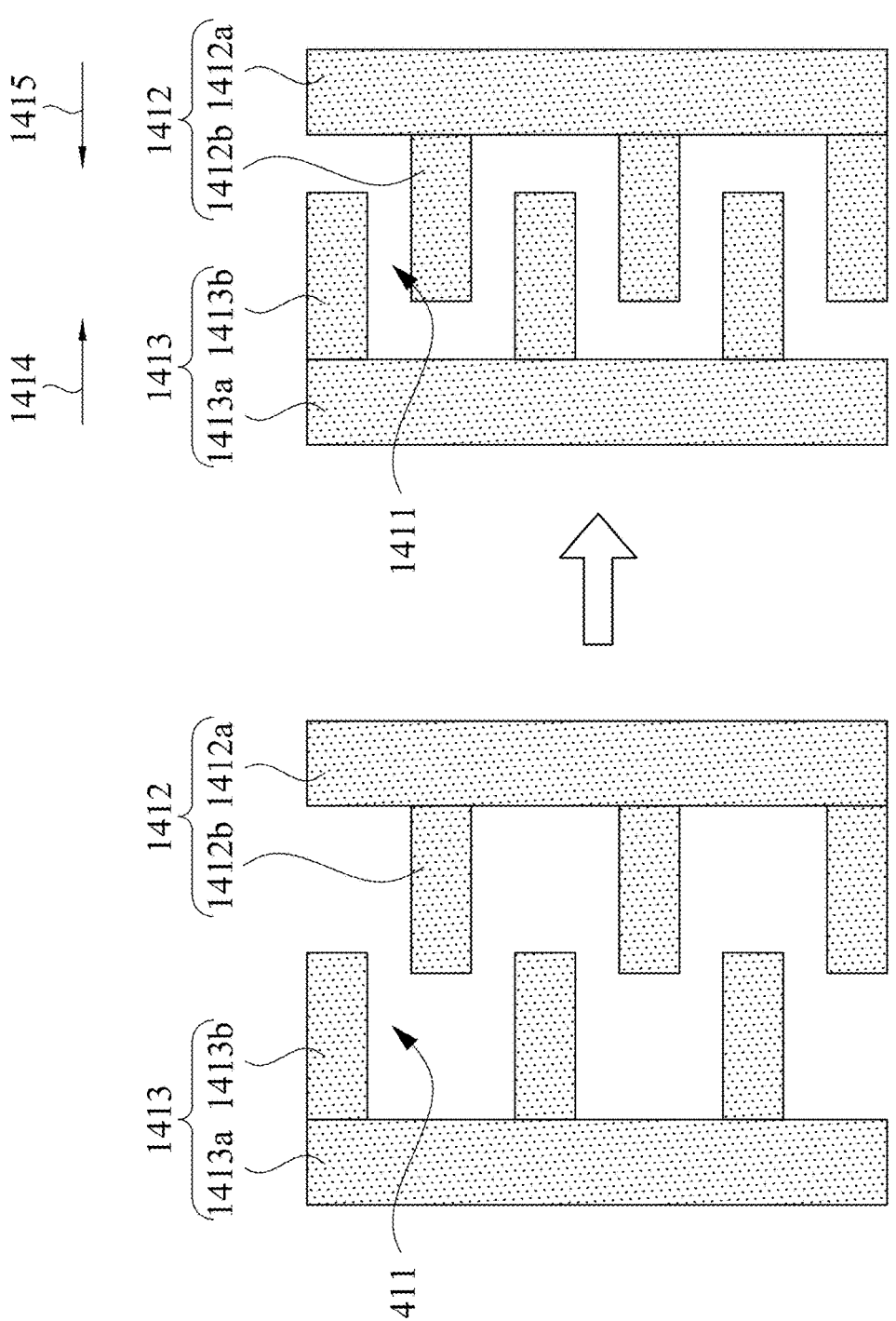
FIGS. 3A to 3C are schematic diagrams of a hollow structure of an implant according to some embodiments of the present disclosure, respectively.

As shown in the schematic diagram of the hollow structure in FIG. 3A, the hollow structure 14 (as shown in FIG. 1A) of the filling portion 12a includes a fence structure 141. In other words, the hollow structure 14 of the filling portion 12a is formed by at least one pair of fence bars 1412 and 1413. The pair of fence bars 1412 and 1413 includes fence handles 1412a and 1413a, and a plurality of fence combs 1412b and 1413b, which are respectively disposed on sides of the fence handles 1412a and 1413a. Each of the fence combs 1412b and each of the fence combs 1413b are arranged alternately. In this way, as shown in the left half of FIG. 3A, when the filling portion 12a is not subjected to force, the pair of fence bars 1412 and 1413 are in an expanded condition, and there are a plurality of voids 1411 between the alternate fence combs 1412b and 1413b. As shown in the right half of FIG. 3A, the when the filling portion 12a is compressed, the pair of fence bars 1412 and 1413 move closer to each other, as shown by arrows 1414 and 1415, the alternate fence combs 1412b and 1413b make the voids 1411 becomes smaller due to the force and is in a collapsed condition.

Figure 3C:
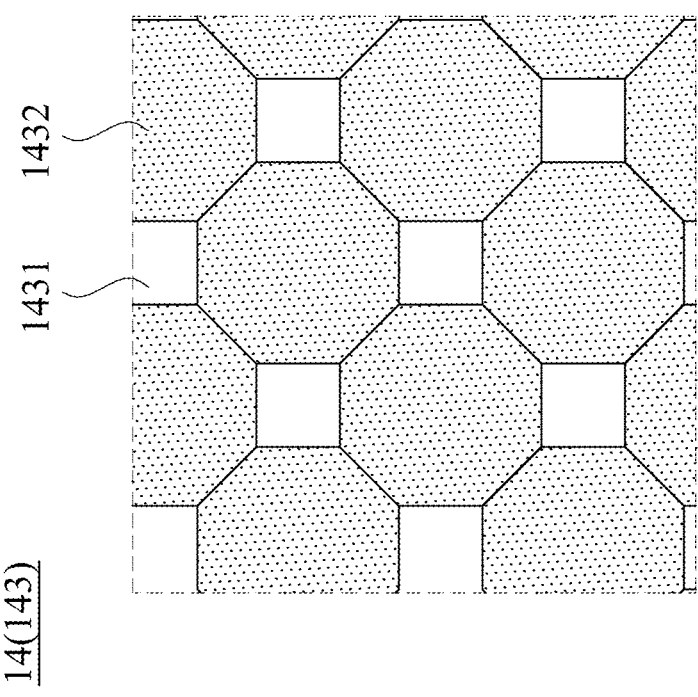
Figure 3B:
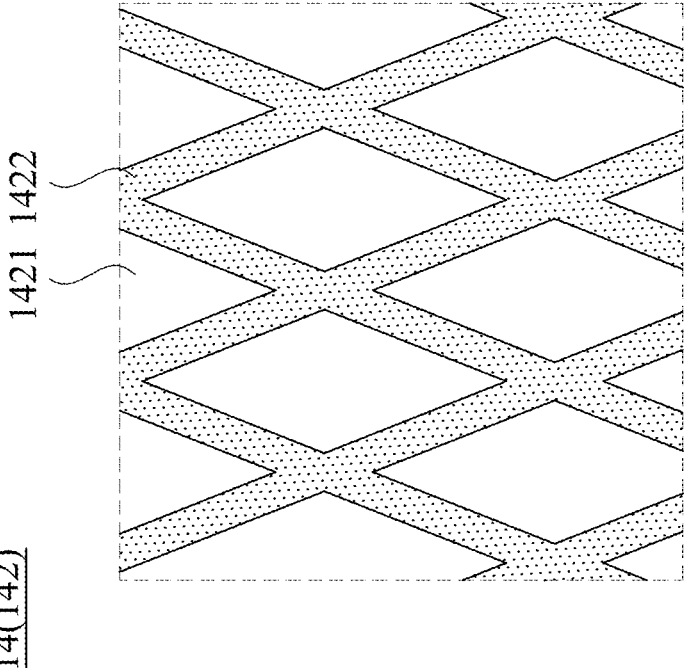

As shown in the schematic diagrams of the hollow structures in FIG. 3B and FIG. 3C, the hollow structure 14 of the filling portion 12a (as shown in FIG. 1A) includes regular grid structures 142 and 143. As shown in FIG. 3B, the regular grid structure 142 is formed by stacking a plurality of linear materials 1422 thereby creating a plurality of voids 1421. The linear materials 1322 include, but are not limited to, powder materials of metals, alloys powders, ceramics powders, and polymeric materials for biomedical applications. In the embodiment of FIG. 3B, a shape of each of the voids 1421 is a quadrilateral, but the shape of each of the voids 1421 may also be a triangle, a rectangle, a polygon or a combination thereof. In addition, in the embodiment of FIG. 3B, a size of each of the voids 1421 is illustrated to be substantially the same, but the size of each of the voids 1421 may also be different. Similarly, when the filling portion 12a is not subjected to an external force, each of the voids 1421 is in an expanded condition, as shown in FIG. 3B, while when the filling portion 12a is subjected to force, each of the voids 1421 is deformed and folded due to the applied force, and in a collapsed condition.

A difference between FIG. 3B and FIG. 3C is that the regular grid structure 143 of FIG. 3C is composed of a plurality of linear materials stacked together to form a plurality of grid bodies 1432, and the grid bodies 1432 enclose to form at least one void 1431. The linear materials 1322 include, but are not limited to, powder materials of metals, alloys powders, ceramics powders, and polymeric materials for biomedical applications. In the embodiment of FIG. 3B, a shape of each of the grid bodies 1432 is an octagon, and the shape of each of the voids 1431 is a quadrilateral, but the shapes of each of the grid bodies 1432 and each of the voids 1431 are not limited thereto. For example, the shape of each of the grid bodies 1432 may also be a triangle, a rectangle, other polygons or a combination thereof, and the shape of each of the voids 1431 may be a triangle, a rectangle, other polygons or a combination thereof. In some embodiments, since the regular grid structure 142 of FIG. 3B is composed of the plurality of linear materials stacked together to form the plurality of voids 1421, and the regular grid structure 143 of FIG. 3C is composed of the plurality of linear materials stacked together to form the plurality of grid bodies 1432 that enclose to form the plurality of voids 1431, a porosity of the filling portion 12a in FIG. 3B is greater than a porosity of the filling portion 12a in FIG. 3C.

In addition, it is understood that to meet the elasticity and stiffness requirements of different portions and/or regions of the implant 1, although not shown in the figures, in some other embodiments, the hollow structure 14 (as shown in FIG. 1A) may also be an irregular grid structure, for example, a shape of each void may be an irregular triangle, quadrilateral, polygon, radial or a combination thereof. Alternatively, the shape of at least one void formed by a plurality of grid bodies is an irregular triangle, quadrilateral, polygon, radial, or a combination thereof. In some other embodiments, the hollow structure 14 includes a fence structure 141, regular grid structures 142 and 143, an irregular grid structure, or a combination thereof.

Second Embodiment

Figure 4:
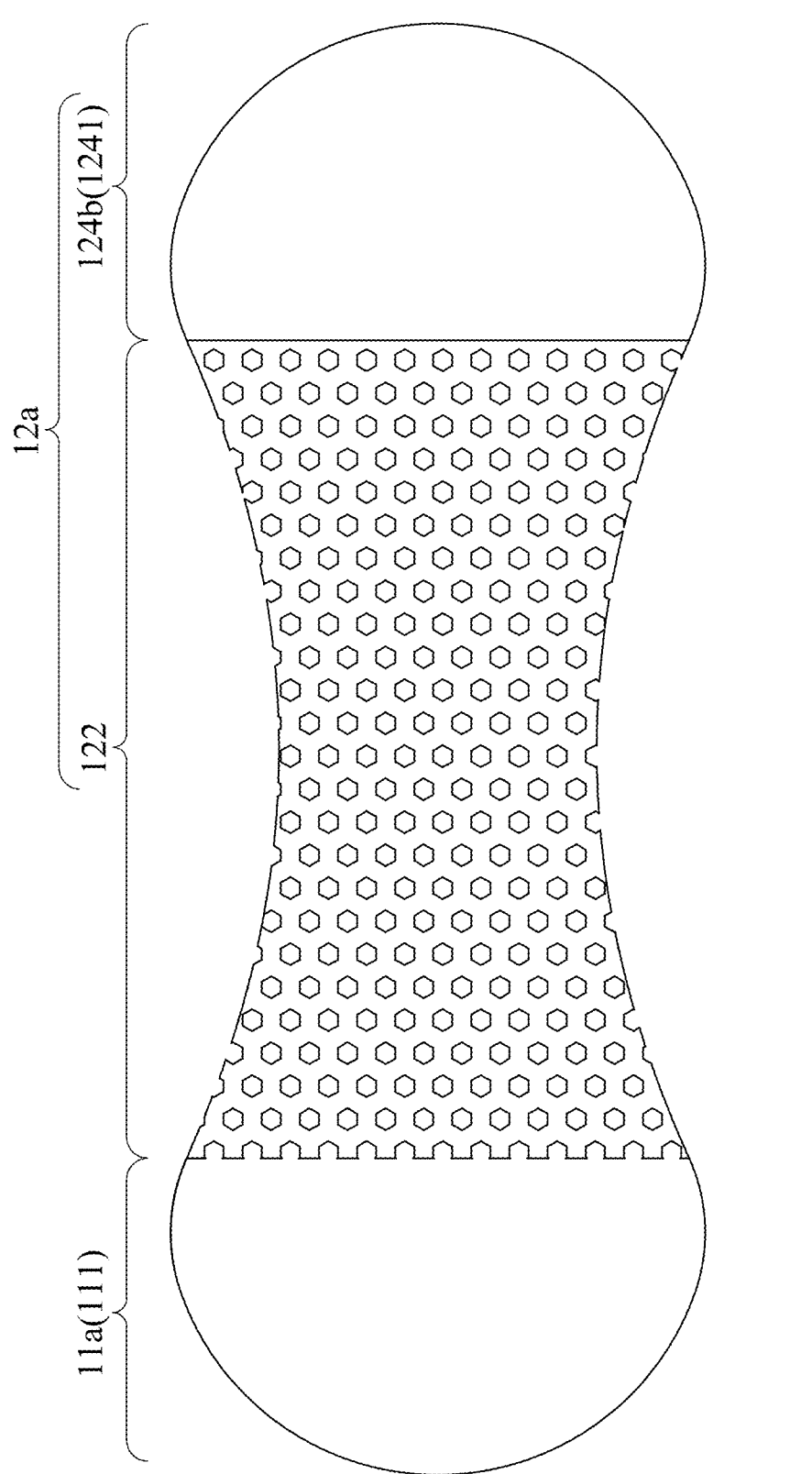
FIG. 4 is a schematic top view of an implant according to a second embodiment of the present disclosure.

Please refer to FIG. 4. FIG. 4 is a schematic diagram of an implant 2 according to a second embodiment of the present disclosure. Differences between the second embodiment and the first embodiment are as follows. The filling portion 12a of the second embodiment disposed at the second end portion P2 (as shown in FIG. 1B) includes a second solid structure 1241. Specifically, an opening portion 124b of the filling portion 12a includes a second solid structure 1241. The second solid structure 1241 is disposed in the opening portion 124b of the filling portion 12a to increase the stiffness of the implant 2. In this way, the fixation of the implant 2 in the cavity is strengthened after the implant 2 is implanted, reducing the risk of displacement. In this embodiment, a ratio of a sum of the solid structures of the first solid structure 111 and the second solid structure 1241 to the elastic structure 121 is in a range of from 1:1 to 1:8.

Similarly, the implant 2 of the second embodiment has similar technical features as described above regarding the implant, the porous structure and/or the hollow structure, the pores and/or the voids, the porosity, and the channel, and not described in detail here.

Third Embodiment

Figure 5:
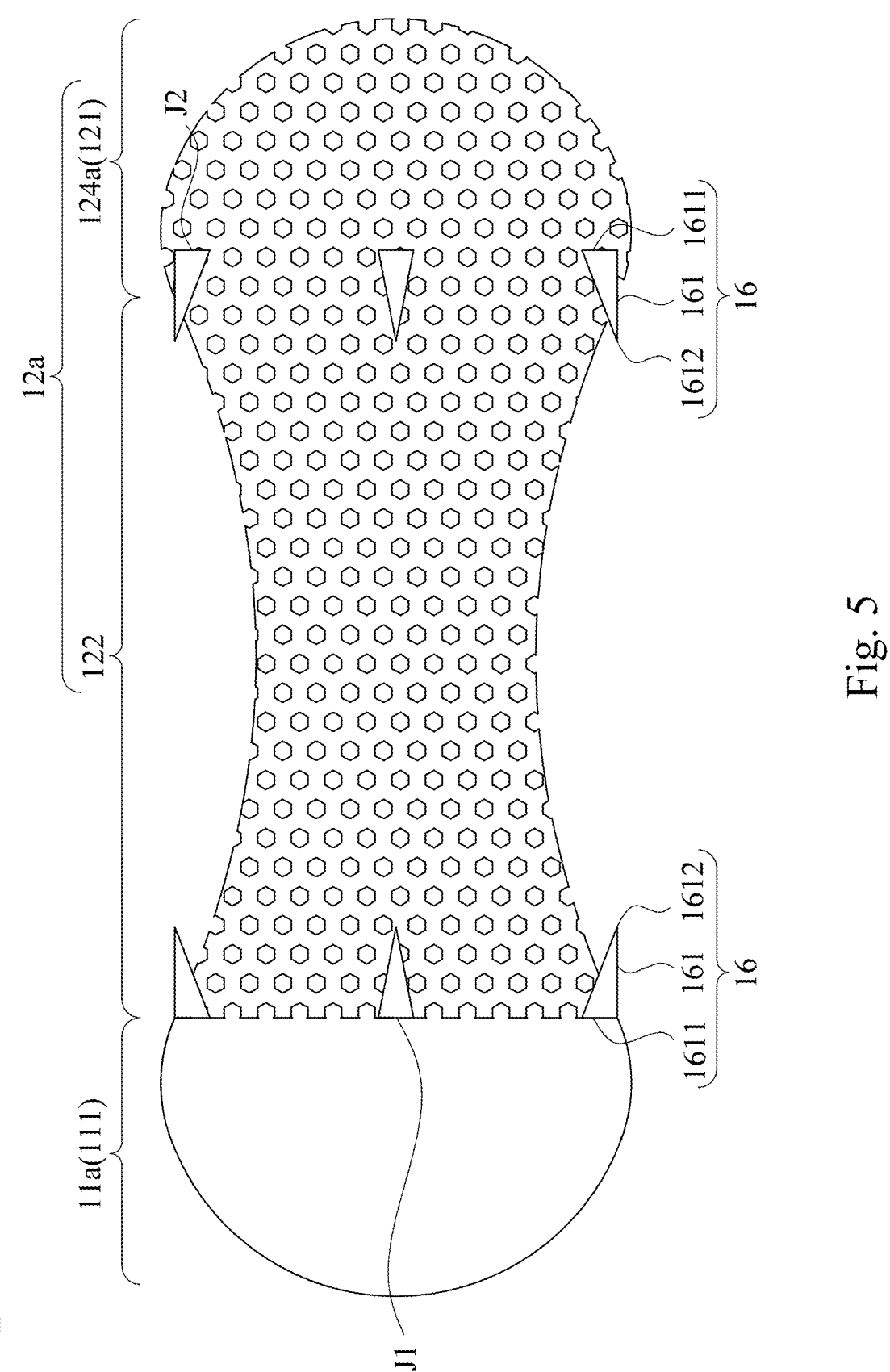
FIG. 5 is a schematic top view of an implant according to a third embodiment of the present disclosure.

Please refer to FIG. 5. FIG. 5 is a schematic diagram of an implant 3 according to a third embodiment of the present disclosure. Differences between the third embodiment and the first embodiment are as follows. An outer surface of a junction J1 of the first end portion P1 and the middle portion P3 (as shown in FIG. 1B) of the implant 3 of the third embodiment includes an anchoring structure 16. The anchoring structure 16 includes at least one barb unit 161. The barb unit 161 includes a fixed end 1611 and a free end 1612, which is positioned opposite to the fixed end 1611. The fixed end 1611 is connected to the outer surface of the junction J1 of the first end portion P1 and the middle portion P3 of the implant 3, while the free end 1612 extends toward a direction of the middle portion P3 of the implant 3. Specifically, the fixed end 1611 is attached to the outer surface of the junction J1 between the limiting portion 11a and the retracted portion 122 of the filling portion 12a. In this embodiment, a number of the barb units 161 is in a range of from 2 to 8. In some other embodiments, the outer surface of the junction J2 between the second end portion P2 and the middle portion P3 of the implant 3, also includes the anchoring structure 16. Similarly, the anchoring structure 16 includes the barb unit 161, and the barb unit 161. The fixed end 1611 is connected to the outer surface of a junction J2 between the second end portion P2 and the middle portion P3 of the implant 3, while the free end 1612 extends toward a direction of the middle portion P3 of the implant 3. Specifically, the fixed end 1611 is connected to the outer surface of the junction J2 between the retracted portion 122 and the opening portion 124a. In this embodiment, the number of the barb units 161 is in the range of from 2 to 8. In the third embodiment, the barb unit 161 includes an arc-shaped barb unit, a wavy barb unit, a circular plate-shaped barb unit, a closed barb unit, an open barb unit or a combination thereof. The anchoring structure 16 is embedded with an inner wall of the cavity to strengthen the fixation of the implant 3 in the cavity, so as to prevent the implant 3 from dislocating.

It is understood that, although not shown in figures, the structure of the third embodiment may also be applied to the implant 2 of the second embodiment (as shown in FIG. 4). As well, in this embodiment, a ratio of a sum of the solid structures of the first solid structure 111 and the second solid structure 1241 to the elastic structure 121 is in a range of from 1:1 to 1:8. Similarly, the implant 3 of the third embodiment has similar technical features as described above regarding the implant, the porous structure and/or the hollow structure, the pores and/or the voids, the porosity, and the channel, and not described in detail here.

Fourth Embodiment

Figure 6:
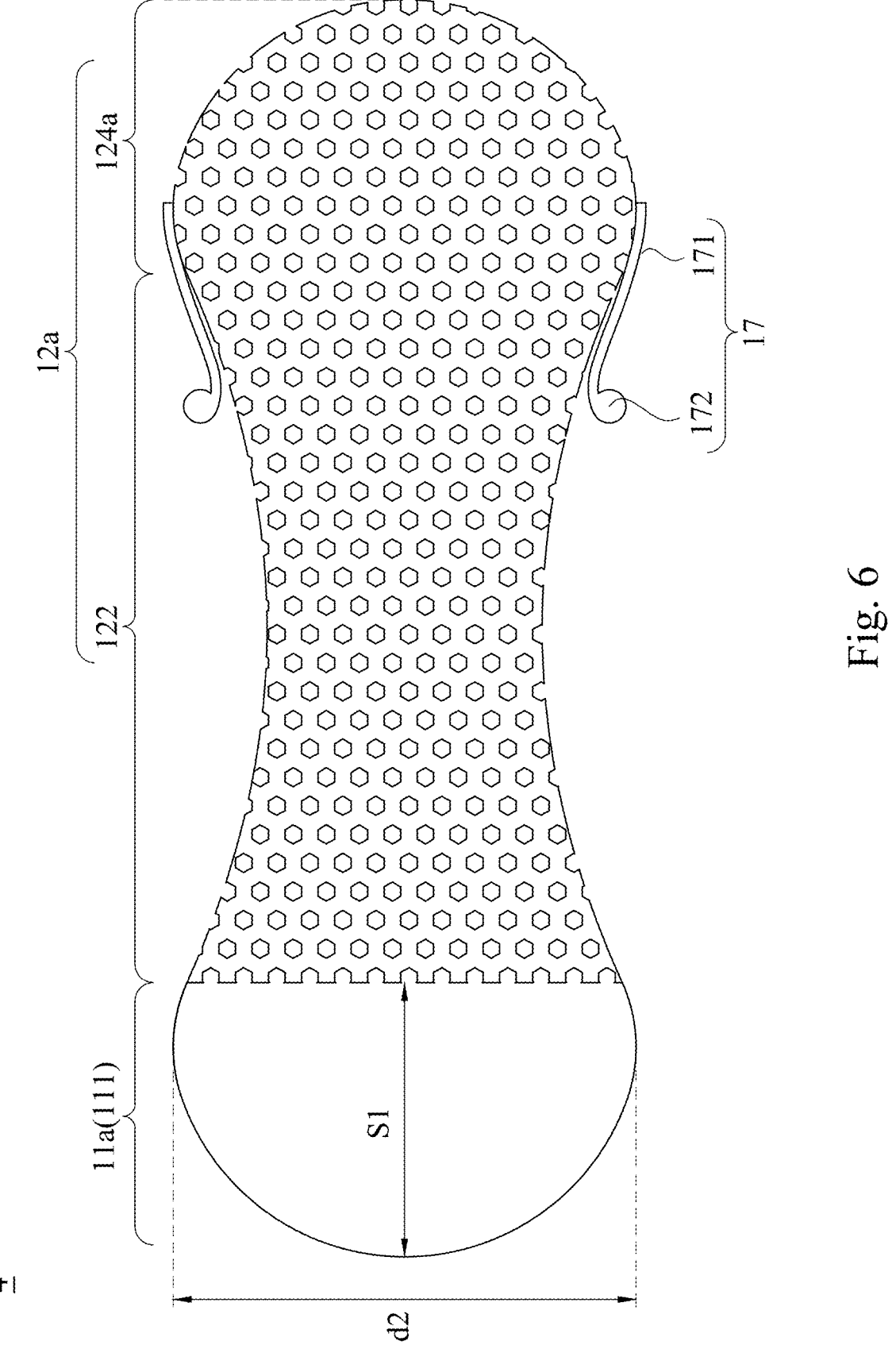
FIG. 6 is a schematic top view of an implant according to a fourth embodiment of the present disclosure.

Please refer to FIG. 6. FIG. 6 is a schematic diagram of an implant 4 according to a fourth embodiment of the present disclosure. Differences between the fourth embodiment and the first embodiment are as follows. The filling portion 12a (such as the opening portion 124a) at the second end portion P2 (as shown in FIG. 1B) of the fourth embodiment includes an against unit 17. The against unit 17 is disposed around an outer surface of the retracted portion 122 and extends to a portion of an outer surface of the opening portion 124a. The against unit 17 includes a connecting rod portion 171 and a limiting against portion 172 integrally formed with the connecting rod portion 171. The against unit 17 is disposed above the outer surface of the retracted portion 122 and the outer surface of the opening portion 124a, and the limiting against portion 172 is spaced from the outer surface of the retracted portion 122. In some embodiments, the connecting rod portion 171 is partially connected to the filling portion 12a, and an area and a length of the connecting rod portion 171 connected to the filling portion 12a may be adjusted based on the implantation requirements. For example, the connecting rod portion 171 is connected to a portion of the outer surface of the opening portion 124a, and the connecting rod portion 171 is partially spaced from a portion of the retracted portion 122. In some embodiments, the against unit 17 is a solid structure. In some embodiments, a number of the against units 17 is in a range of from 2 to 8. In some embodiments, the against unit 17 may be symmetrically disposed on the outer surface of a portion of the retracted portion 122 and a portion of the opening portion 124a.

In this embodiment, when the implant 4 is implanted, the limiting against portion 172 of the against unit 17 is pressed against the outer surface of the retracted portion 122 due to the applied force. Then, after the implant 4 is implanted, the limiting against portion 172 releases elastic energy to strengthen the fixation of the implant 4 in the cavity.

It is understood that, although not shown in figures, the structure of the fourth embodiment may also be applied to the implant 2 of the second embodiment (as shown in FIG. 4). In this embodiment, a ratio of a sum of the solid structures of the first solid structure 111 and the second solid structure 1241 to the elastic structure 121 is in a range of from 1:1 to 1:8. Similarly, the implant 4 of the fourth embodiment has similar technical features as described above regarding the implant, the porous structure and/or the hollow structure, the pores and/or the voids, the porosity, and the channel, and not described in detail here.

Fifth Embodiment

Figure 7:
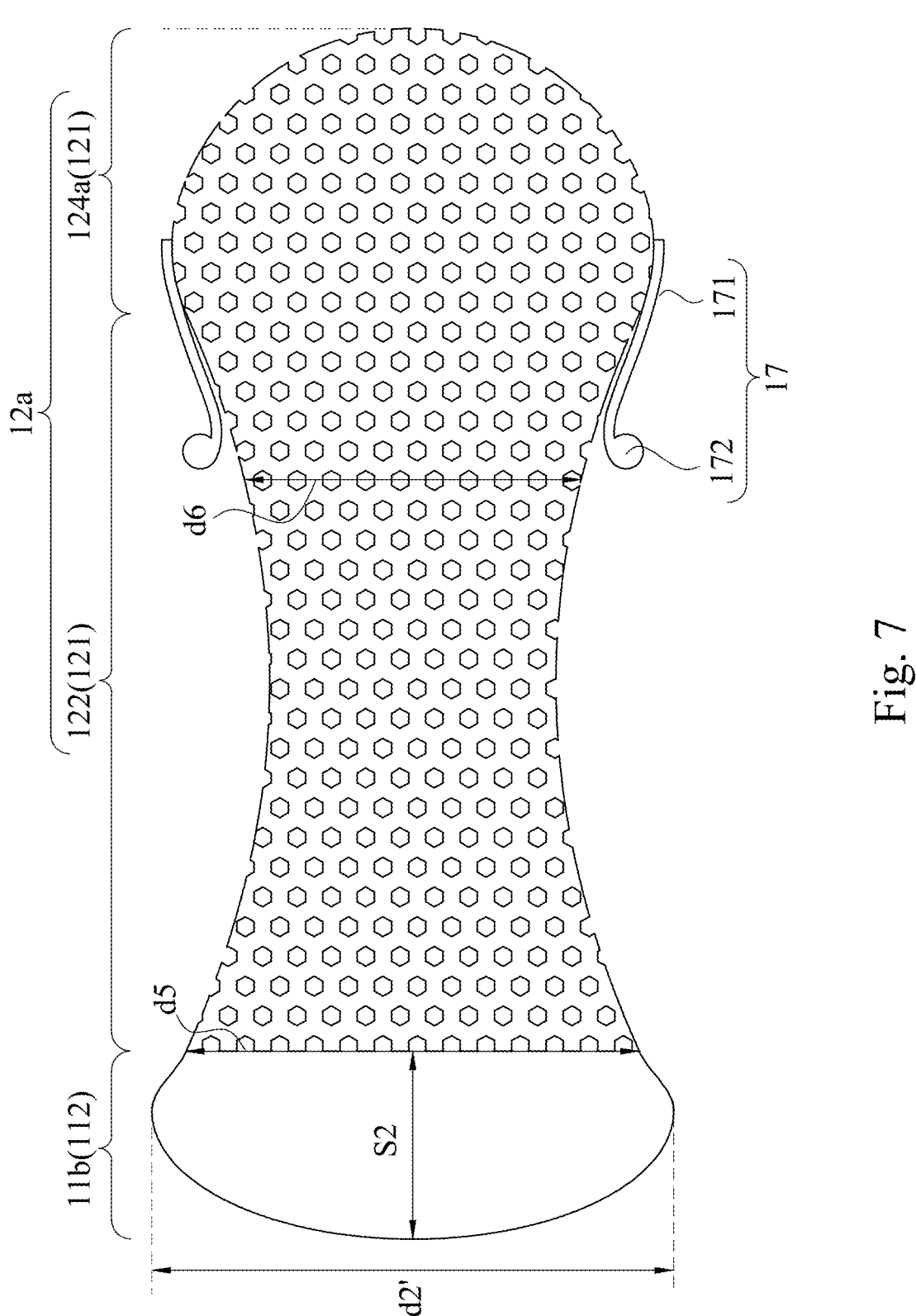
FIG. 7 is a schematic top view of an implant according to a fifth embodiment of the present disclosure.

Please refer to FIG. 7. FIG. 7 is a schematic diagram of an implant 5 according to the fifth embodiment of the present disclosure. Differences between the fifth embodiment and the fourth embodiment are as follows. A shape of the limiting portion 11b of the fifth embodiment is a disc-shaped structure, and a limiting portion 11b includes a first solid structure 112. Specifically, the round cake shape of the limiting portion 11b is a hemispherical shape, and the limiting portion 11b has a curved surface on the other side of the limiting portion 11b opposite to one side of the limiting portion 11b connected to the retracted portion 122. Through the material properties and material stiffness of the first solid structure 111 (as shown in FIG. 6) of the implant 4, the first solid structure 111 is deformed to form the first solid structure 112 of the fifth embodiment. Therefore, a distance S1 of the first solid structure 111 is compressed to a distance S2 of the first solid structure 112 due to the applied force. Moreover, the maximum diameter d2 (as shown in FIG. 6) of the first solid structure 111 is reduced to a diameter d2', and the diameter d2' refers to a maximum diameter of the first solid structure 112. In this way, a radial supporting force of a side of the implant 5 may be greater than a radial supporting force of a side of the implant 4, improving the fixation effect. In addition, since the force absorbed by the limiting portion 11b is relatively small when the implant 5 is implanted, a reaction force acting on the limiting portion 11b increases after the implant 5 is implanted. Further, the against unit 17 does not excessively displace due to the force released by the elastic energy. As a result, the implant 5 of the fifth embodiment may increase the reaction force and reduce the displacement, thereby improving the stability of the implant 5 when subjected to force or when compressed within the cavity.

It is understood that, although not shown in figures, the structure of the fifth embodiment may also be applied to the implant 2 of the second embodiment (as shown in FIG. 4). In this embodiment, a ratio of a sum of the solid structures of the first solid structure 112 and the second solid structure 1241 to the elastic structure 121 is in a range of from 1:1 to 1:8. Similarly, the implant 5 of the fifth embodiment has similar technical features as described above regarding the implant, the porous structure and/or the hollow structure, the pores and/or the voids, the porosity, the channel, and the against unit, and not described in detail here.

Sixth Embodiment

Figure 8:
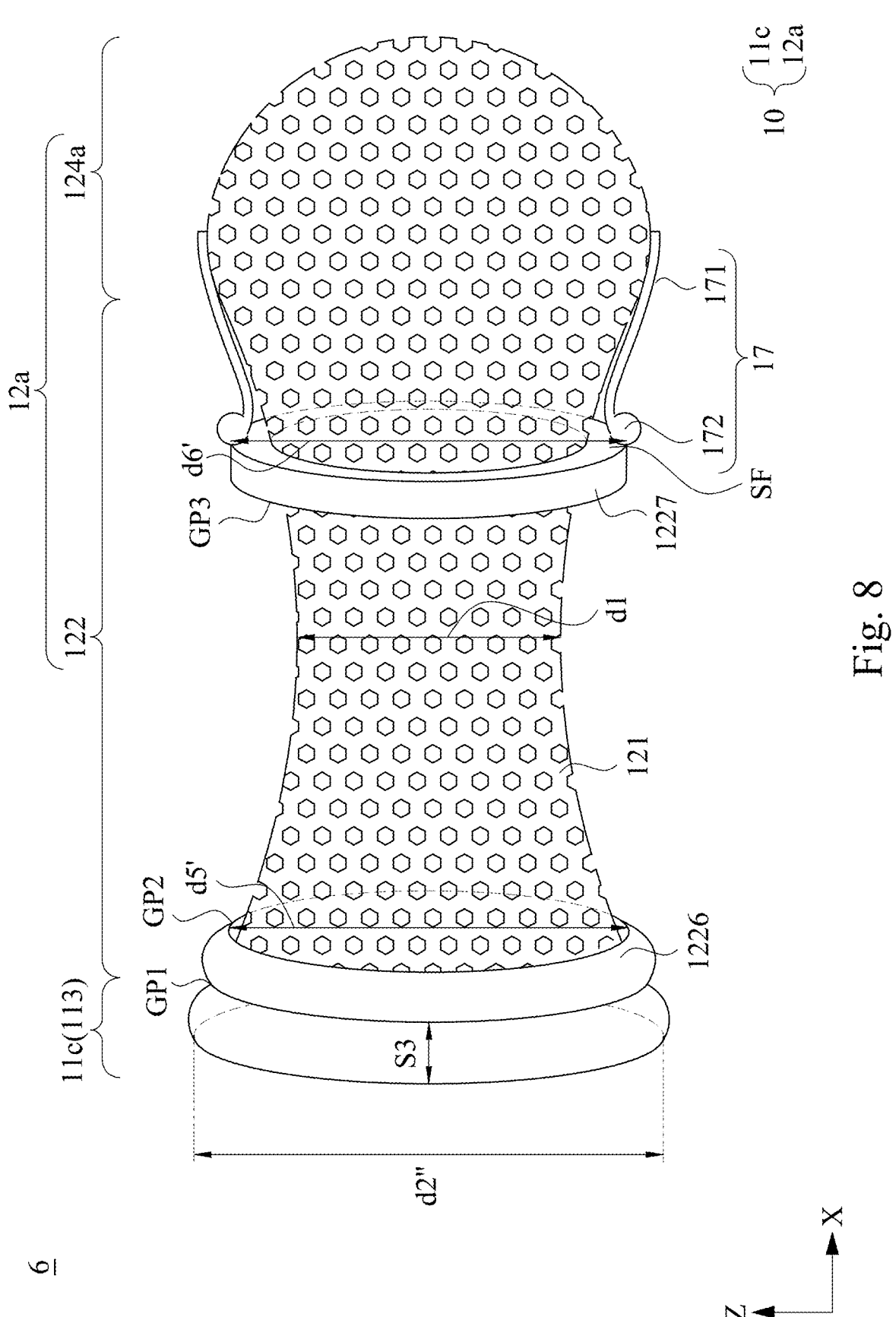
FIG. 8 is a schematic diagram of an implant according to a sixth embodiment of the present disclosure.

Please refer to FIG. 8. FIG. 8 is a schematic diagram of an implant 6 according to a sixth embodiment of the present disclosure. Differences between the sixth embodiment and the fifth embodiment are as follows. The retracted portion 122 of the sixth embodiment further includes a third solid structure 1226 and a fourth solid structure 1227. Similarly, through the material properties and material stiffness of the first solid structure 112 of the implant 5 (as shown in FIG. 7), the first solid structure 112 is deformed to form the first solid structure 113 of the sixth embodiment. Therefore, the distance S2 of the first solid structure 112 is compressed to a distance S3 of the first solid structure 113. Moreover, the maximum diameter d2 of the first solid structure 111 (as shown in FIG. 7) is reduced to a diameter d2" of the first solid structure 113, and the diameter d2" refers to a maximum diameter of the first solid structure 113. In this way, a radial supporting force of a side of the implant 6 may be greater than the radial supporting force of the side of the implant 5, thereby improving the fixation effect.

The third solid structure 1226 has a diameter d5', and the diameter d5' refers to the maximum diameter of the third solid structure 1226. Similar to the above, compared with a diameter d5 of a first end of the retracted portion 122 connected to the limiting portion 11b in the fifth embodiment (as shown in FIG. 7), the diameter d5' of the third solid structure 1226 becomes greater due to force. In some embodiments, the diameter d2" of the first solid structure 113 is greater than the diameter d5' of the third solid structure 1226. A first end of the third solid structure 1226 is adjacent to the limiting portion 11c, while a second end of the third solid structure 1226 is connected to the elastic structure 121 of the retracted portion 122. Although the third solid structure 1226 of FIG. 8 is illustrated as being connected to the first solid structure 113 of the limiting portion 11c, the third solid structure 1226 may also be spaced from the first solid structure 113 of the limiting portion 11c. In addition, since the first solid structure 113 and the third solid structure 1226 protrude longitudinally relative to the body 10, for example, protrude along a Z direction. A groove pattern GP1 is disposed between the first solid structure 113 and the third solid structure 1226, and a groove pattern GP2 is disposed between the third solid structure 1226 and the retracted portion 122. By incorporating the groove patterns GP1 and GP2, an implantation resistance may be increased to prevent the implant 6 from dislocating.

The fourth solid structure 1227 has a diameter d6', and the diameter length d6' refers to the maximum diameter of the fourth solid structure 1227. Similar to the above, compared with a diameter d6 of the retracted portion 122 close to the limiting against portion 172 in the fifth embodiment (as shown in FIG. 7), the diameter d6' of the fourth solid structure 1227 becomes greater due to deformation. The diameter d6' of the fourth solid structure 1227 is greater than the minimum diameter d1 of the retracted portion 122. The fourth solid structure 1227 is adjacent to the limiting against portion 172, and a diameter d4 of the fourth solid structure 1227 is greater than the minimum diameter d1 of the retracted portion 122. Although the fourth solid structure 1227 in FIG. 8 is illustrated as being connected to the limiting against portion 172, the fourth solid structure 1227 may also be spaced apart from the limiting against portion 172. In some embodiments, the limiting against portion 172 may press against a surface SF of the fourth solid structure 1227 after receiving force. A groove pattern GP3 is disposed between the fourth solid structure 1227 and the elastic structure 121 of the retracted portion 122. In this way, by incorporating the groove pattern GP3, the implantation resistance can be increased to prevent the implant 6 from dislocating. Although in the embodiment of FIG. 8, a number of groove patterns GP1, GP2, and GP3 is three, other numbers may be used as long as the effect of increasing the implantation resistance to prevent the implant from dislocating can be achieved. In this embodiment, a ratio of a sum of the solid structures of the first solid structure 113, the third solid structure 1226, and the fourth solid structure 1227 to the elastic structure 121 is in a range of from 1:1 to 1:8.

Similarly, since the force absorbed by the elastic structure is relatively minimal when the implant 6 is implanted, the force acting on the first solid structure 113 of the limiting portion 11c and the third solid structure 1226 of the retracted portion 122 increases after the implant 6 is implanted. Moreover, through the against unit 17, the excessive displacement may be prevented after the implant 6 is implanted. As a result, the implant 6 of the sixth embodiment may increase the reaction force and reduce the displacement, so as to improve the stability of the implant 6 when subjected to force or extruded in the cavity.

It is understood that, although not shown in figures, the structure of the sixth embodiment may also be applied to the implant 2 of the second embodiment (as shown in FIG. 4). In this embodiment, a ratio of a sum of the solid structures of the first solid structure 113, the third solid structure 1226, and the fourth solid structure 1227 to the elastic structure 121 is in a range of from 1:1 to 1:8. Similarly, the implant 2 of the second embodiment has similar technical features as described above regarding the implant, the porous structure and/or the hollow structure, the pores and/or the voids, the porosity, the channel, and the against unit, and not described in detail here.

Seventh Embodiment

Figures 9A, 9B:
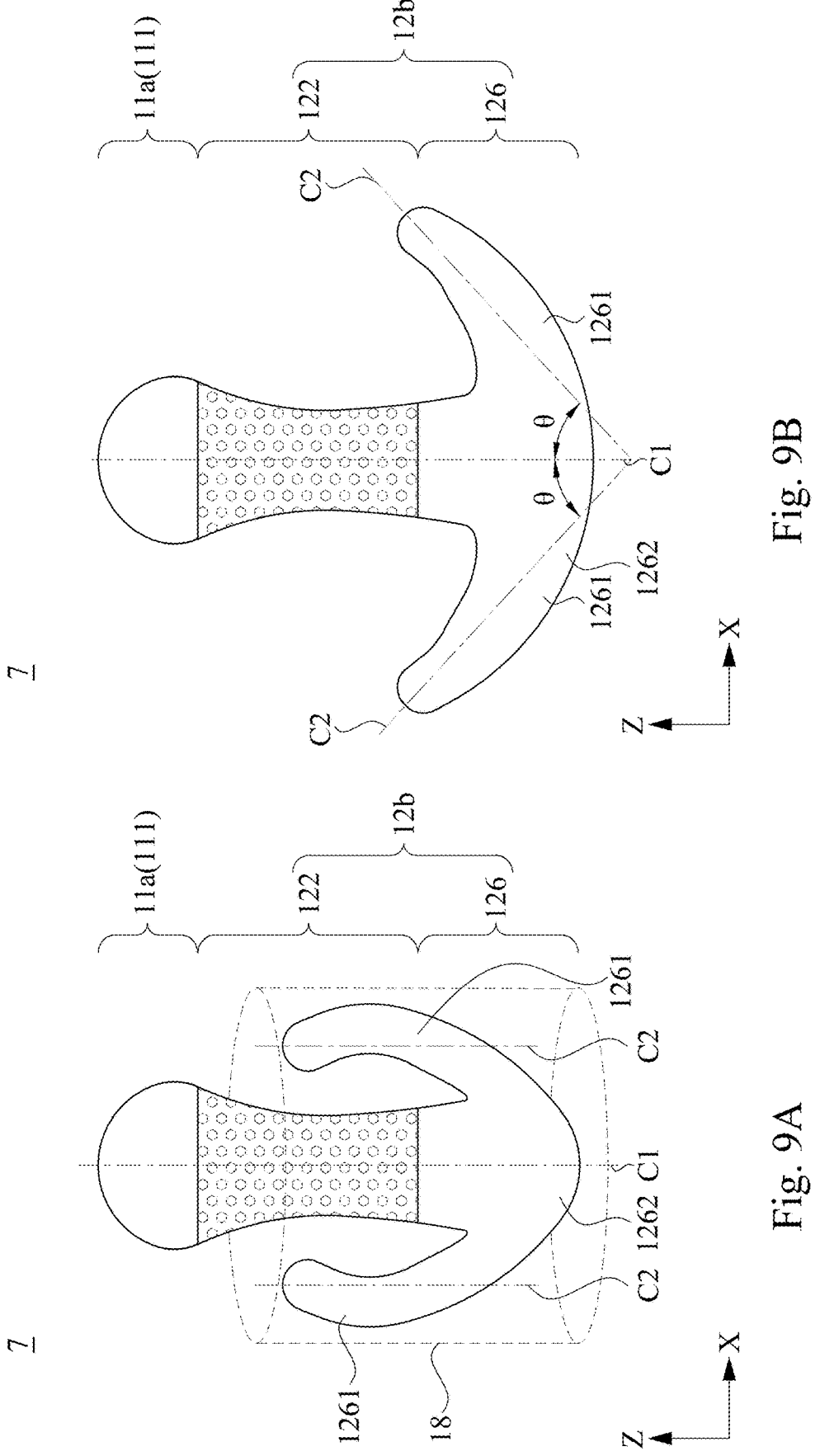
FIG. 9A is a side view of an implant in a collapsed condition according to a seventh embodiment of the present disclosure.
FIG. 9B is a side view of an implant in an expanded condition according to the seventh embodiment of the present disclosure.
Figure 9C:
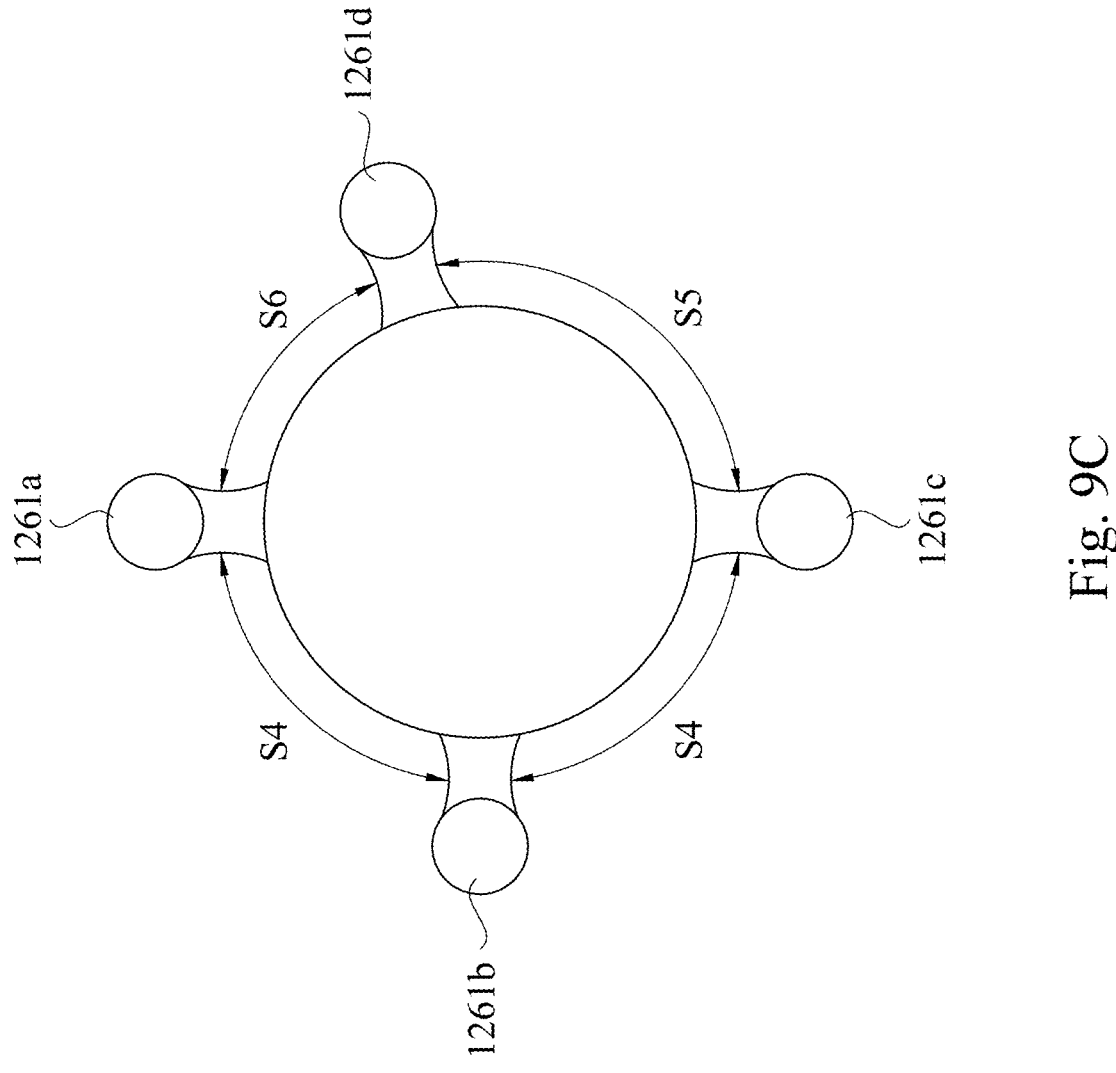
FIG. 9C is a schematic top view of opening portions of an implant according to a seventh embodiment of the present disclosure.

Please refer to FIGS. 9A and 9B. FIG. 9A is a schematic diagram of the implant 7 in a collapsed condition according to the seventh embodiment of the present disclosure, and FIG. 9B is a schematic diagram of the implant 7 in an expanded condition according to the seventh embodiment of the present disclosure. Differences between the seventh embodiment and the second embodiment are as follows. An opening portion 126 of the filling portion 12b of the seventh embodiment includes at least two arms 1261, and each of the arms 1261 has a fixed end and an open end. The fixed end of each of the arms 1261 is connected to an outer surface of a bottom 1262 of the opening portion 126, while the open end of each of the arms 1261 extends a direction from the bottom 1262 of the opening portion 126 toward the limiting portion 11a, such as extending toward the Z direction. The at least two arms 1261 are arranged around an outer periphery of the opening portion 126. In the side view, the at least two arms 1261 are laterally collapsed or expanded relative to a central axis C1 of the opening portion 126. Specifically, as shown in FIG. 9A, when the implant 7 is in the collapsed condition, for example, the implant 7 is folded in a sleeve 18, central axes C2 of the at least the two arms 1261 is respectively substantially parallel to the central axis C1 of the opening portion 126, that is, the central axes C2 of the at least the two arms 1261 are substantially parallel to a Z axis. In addition, the implant 7 being folded into the sleeve 18 is merely an exemplary embodiment of the collapsed condition of the present disclosure, and the present disclosure is not limited thereto. As well, the implant 7 may also be folded in other ways. When the opening portion 126 of the implant 6 is expanded, the at least the two arms 1261 expand clockwise or counterclockwise from the Z axis toward the X axis. As shown in FIG. 9B, when the implant 7 is in the expanded condition, there is an angle θ between the central axes C2 of the at least two arms 1261 and the central axis C1 of the opening portion 126, respectively. That is, there is the angle θ between the at least two arms 1261 and the Z axis. In some embodiments, the angle θ is in a range of from 1 degree to 90 degrees.

In some embodiments, the at least two arms 1261 may be arranged around an outer periphery of the opening portion 126 of the implant 7. In some embodiments, a number of the at least two arms 1261 is in a range of from 2 to 8. Please refer to the top view of FIG. 9C. In this exemplary embodiment, when viewed from top, the opening portion 126 is substantially circular, but may also be other shapes, such as an ellipse, and the present disclosure is not limited thereto. When there are four arms 1261a, 1261b, 1261c, and 1261d, with a center C3 of the opening portion 126 as a center, a circumference S4 between the arm 1261a and the arm 1261b and the circumference S4 between the arm 1261b and the arm 1261c are identical. In other words, the arms 1261a, 1261b, and 1261c are equidistantly arranged around the outer periphery of the opening portion 126 of the implant 7. Moreover, with the center C3 of the opening portion 126 as the center, the circumference S4 between the arms 1261b and the arm 1261c and a circumference S5 between the arm 1261c and the arm 1261d are different, and a circumference S6 between the arm 1261a and the arm 1261d and the circumference S5 between the arm 1261c and the arm 1261d are different. In other words, the arms 1261b, 1261c, and 1261d are unequally disposed around the outer periphery of the opening portion 126 of the implant 7, and the arms 1261a, 1261c, 1261d are unequally disposed around the outer periphery of the opening portion 126 of the implant 7. The exemplary embodiment is simple an example, and the present disclosure is not limited thereto.

It is understood that, although not shown in figures, the structure of the seventh embodiment may also be applied to the implant 1 of the first embodiment (as shown in FIG. 1A)

and/or the implant 3 of the third embodiment (as shown in FIG. 5). Similarly, the implant 7 of the seventh embodiment has similar technical features as described above regarding the implant, the porous structure and/or the hollow structure, the pores and/or the voids, the porosity, and the channel, and not described in detail here.

The implants of various embodiments disclosed herein (such as the implants 1, 2, 3, 4, 5, 6, 7) may be configured to be used in the field of regenerative medicine, for example spinal cord injury-related surgery, such as repair surgery of intervertebral disc damage, etc., anchoring and providing regenerative materials for bone-related surgeries, such as arthroscopic surgery and cartilage regeneration and repair surgery, etc., anchoring and providing regenerative materials for heart-related surgeries, intraocular tissue repair or protection-related surgery, such as heart valve surgery, or nasal embolization-related surgery.

Figure 10:
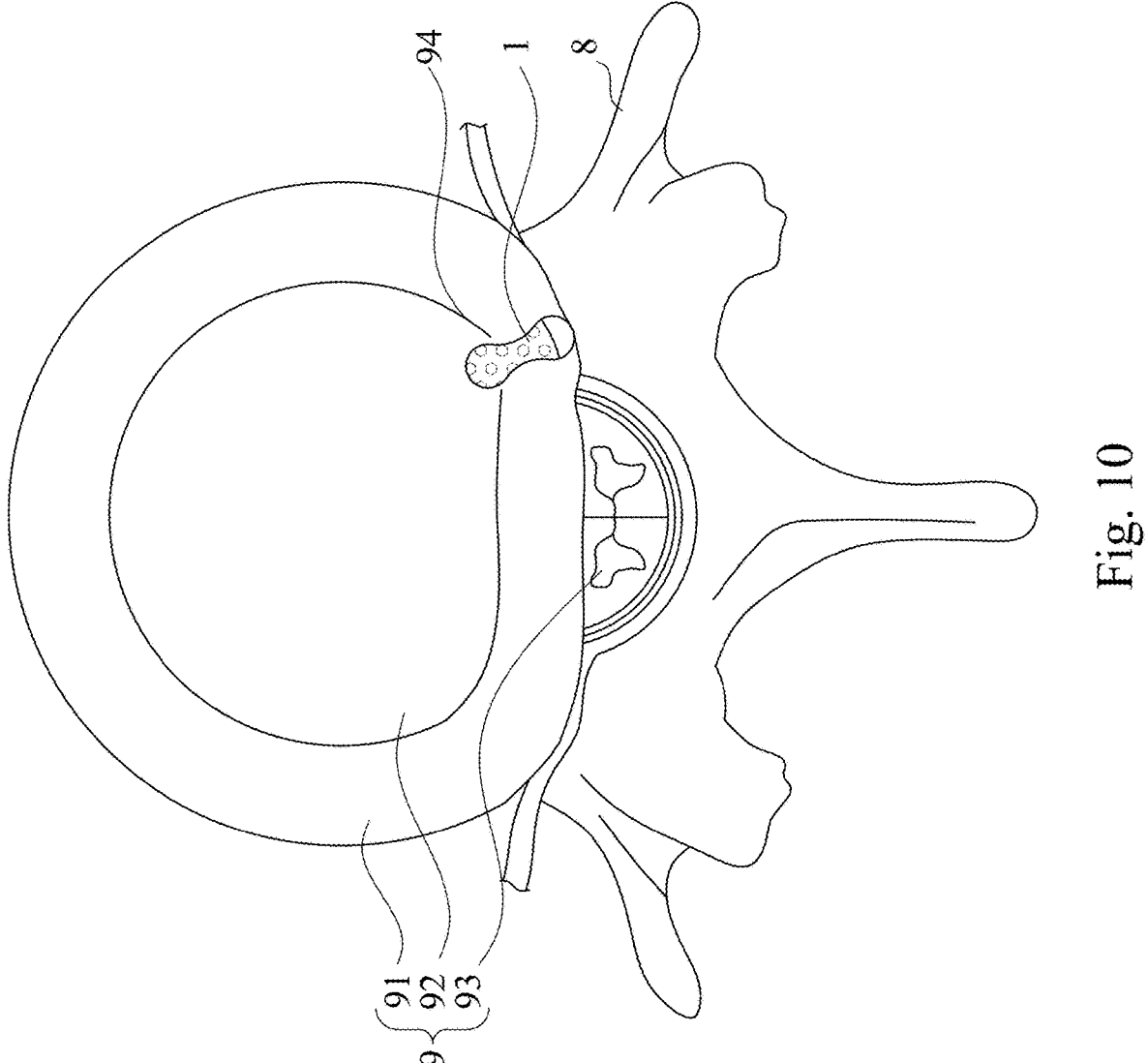
FIG. 10 is a schematic diagram illustrating a condition of use of an intervertebral disc injury repair surgery as an example according to some embodiments of the present disclosure.

In order to enable a person having ordinary skill in the art to which the present disclosure pertains to more clearly understand the embodiments of the present disclosure, please refer to FIG. 10. FIG. 10 is a schematic diagram of an example of a repair surgery for intervertebral disc damage according to some embodiments of the present disclosure.

As shown in the top view of FIG. 10, an intervertebral disc 9 is a structure located between two vertebrae 8 and is responsible for force dispersion. An outer layer of the intervertebral disc 9 is composed of an annulus fibrosus 91 formed by a plurality of layers of collagen fibers, and a center of the annulus fibrosus 91 is composed of a nucleus pulposus 92. However, when the annulus fibrosus 91 is slightly damaged and becomes locally fragile (such as a damaged site 94), the nucleus pulposus 92 in the intervertebral disc 9 is prone to extrusion toward the damaged site 94 and bulge, and further protrude, which is the so-called "herniated intervertebral disc." Additionally, whether bulging or protruding, dura mater and nerves 93 may be compressed, causing neurological symptoms such as pain or numbness and weakness in patients.

The implants of various embodiments of the present disclosure can provide a means of filling the damaged annulus fibrosus, and FIG. 10 takes the implant 1 of the first embodiment as an example, but the present disclosure is not limited thereto. After the protruding portion of the intervertebral disc is removed, the implant 1 is implanted at the damaged site 94 to create a mechanical support space to fill the cavity of the damaged site 94 of the annulus fibrosus 91. In this way, in addition to preventing the leakage of the nucleus pulposus 92, some tissues that still have functions of the intervertebral disc 9 may be retained. Furthermore, as mentioned above, each of the implants of the various embodiments of the present disclosure includes the porous structure, and the porous structure can provide a regenerative structure to regenerate and repair the tissues of the intervertebral disc 9. Thus, the implants of the various embodiments of the present disclosure can prevent postoperative degeneration and re-herniation of herniated intervertebral disc.

Further, biomechanical testing was performed to understand a maximum destructive strength that the implant can withstand after being implanted into a cavity. This test subjected Experimental Group 1 and Experimental Group 2 in a cavity polymer for static compression bending test complied with the American Society for Testing and Materials (ASTM) implant fatigue test standards.

Firstly, a manufacturing method of the implants of the Experimental Group 1 and Experimental Group 2 is described as follows. The implants were manufactured 3-dimension (3D) printing using additive manufacturing (AM) process technology and made of polyetheretherketone (PEEK) polymer materials.

In Experimental Group 1, an artificial synthetic bone was used to simulate the vertebra, and an artificial annulus fibrosus was used to simulate the intervertebral disc. A material of the artificial synthetic bone included polyurethane foam block with a density of 0.32 g/c.c. (i.e. 20 pcf), a compressive strength of 8.4 MPa, a tensile strength of 5.6 MPa, and a shear strength of 4.3 MPa. A material of the artificial annulus fibrosus included polysiloxane with a density of 1200 kg/m$^3$ and a Young's modulus of 2.69 MPa. In Experimental Group 2, the implant of the first embodiment of the present disclosure was placed in a vertebra of a pig.

The biomechanical testing of the present disclosure is described with Experimental Group 1. A simulation test was carried out using an MTS universal material testing machine (Instron 5900R, USA). The implant of the first embodiment was placed in the simulated cavity of the artificial annulus fibrosus, and the artificial synthetic bone was used as an upper test block and a lower test block. Next, the simulated cavity placed with the implant of Experimental Group 1 was placed between the upper test block and the lower test block. The upper test block and the lower test block were in contact with an upper surface and a lower surface of the simulated cavity, respectively, and the simulated cavity was disposed between the upper test block and the lower test block without displacing.

Two stages of force (unit: Newton (N)) were applied to Experimental Group 1 through the upper test block to understand the destructive strength that the implant could withstand after being implanted into the cavity. In the first stage, before applying the force, a distance between the upper test block and the lower test block was 10 mm. When the compression reached 30% of a limited displacement, that is, when the limited displacement was 3 mm (i.e., when the distance between the upper test block and the lower test block compressed from 10 mm to 7 mm), the force at the displacement point was recorded. In the second stage, the force was applied to the cavity with the implant for compressing to its limit. In this experiment, before applying the force, the distance between the upper test block and the lower test block is 10 mm. When compressed to the limit, an ultimate displacement was 6 mm, that is, when the distance between the upper test block and the lower test block compressed from 10 mm to 4 mm, the force at the displacement point was recorded. In addition, Experimental Group 2 was also tested in a similar means, which will not be repeated here.

After biomechanical testing of Experimental Group 1, it was found that under normal pressure, the implant could withstand 623.4±2.5 N in the simulated cavity without dislocating, and the maximum pressure could reach 2226.7±24.0 N without dislocating. The biomechanical testing of Experimental Group 2 with the pig showed that the implant in the cavity of vertebra of the pig could withstand the maximum pressure 2149.51±146.33 N without dislocating and leaking of nucleus pulposus when the displacement was 4.81±1.61 mm.

Experimental Group 1 shows that under normal pressure, the implant can withstand 623.4±2.5 N in the simulated cavity without dislocating, while the normal pressure that the vertebrae of an adult can withstand is about 800 N. As a result, it can be seen that after the implant is implanted in the cavity, it is not prone to dislocating, and the effect of preventing the liquid in the cavity from flowing out can also be achieved.

As stated above, traditional bone implants are mainly used for filling and locking, and the traditional bone implants may cause the risk of loosening and falling due to excessive stiffness when these bone implants are applied to soft tissues. Currently, bone implants are not used in clinical practice for intervertebral disc repair. In clinical cases, they are left untreated or simply sutured. Therefore, each embodiment of the present disclosure can change the material stiffness of the implant by adjusting the ratio of the solid structure to the non-solid structure of the implant, so as to increase the contact between the implant and the cavity. Moreover, the pressure inside and outside the cavity is balanced through the implant, the fixation of the implant can be strengthened. In this way, on one hand, the implant is not vulnerable to dislocate from the cavity; on the other hand, fluid leakage from the cavity can be prevented.

While the disclosure has been described and illustrated with reference to specific embodiments thereof, these descriptions and illustrations do not limit the disclosure. It should be understood by those skilled in the art that various changes may be made and equivalents may be substituted without departing from the true spirit and scope of the disclosure as defined by the appended claims. Accordingly, the scope of the present disclosure shall be determined by the scope of the accompanying claims.

What is claimed is:

1. An implant for repairing an intervertebral annulus fibrosus, comprising:
    a body having a first end portion, a second end portion, and a middle portion disposed between the first end portion and the second end portion;
    a limiting portion comprising a first solid structure and being located at the first end portion; and
    a filling portion comprising an elastic structure and a porous structure in the elastic structure, and being located between the middle portion and the second end portion, wherein the elastic structure comprises:
        a first region adjacent to the first end portion and having a first porosity;
        a second region adjacent to the second end portion and having a second porosity; and
        a third region disposed between the first region and the second region and having a third porosity,
        wherein the third porosity of the third region is greater than the first porosity of the first region,
    wherein a ratio of the first solid structure to the elastic structure is in a range of from 1:1 to 1:8; and
    wherein a diameter of the first end portion of the body is greater than a diameter of the middle portion, and a diameter of the second end portion is greater than the diameter of the middle portion.

2. The implant of claim 1, wherein the porous structure comprises a hole structure, a regular grid structure, an irregular grid structure, or a combination thereof.

3. The implant of claim 2, wherein the porous structure is a gradient porous structure.

4. The implant of claim 1, wherein pore sizes of a plurality of pores in the porous structure are in a range of from 200 micrometers to 600 micrometers.

5. The implant of claim 1, further comprising:
    a channel disposed within the body of the implant and extending through the body.

6. The implant of claim 1, wherein the third porosity is greater than both the first porosity and the second porosity.

7. The implant of claim 1, wherein the filling portion further comprises a hollow structure.

8. The implant of claim 7, wherein the hollow structure comprises a fence structure, a regular grid structure, or a combination thereof.

9. The implant of claim 1, wherein an outer surface of a junction between the first end portion and the middle portion of the implant comprises an anchoring structure, and the anchoring structure comprises at least one barb unit, and
    the at least one barb unit comprises a fixed end and a free end opposite to the fixed end, and the fixed end is connected to the outer surface of the junction, and the free end extends toward a direction of the middle portion of the implant.

10. The implant of claim 1, wherein the filling portion located at the second end portion comprises a second solid structure.

11. The implant of claim 1, wherein the filling portion further comprises:
    a retracted portion having a first end and a second end opposite to the first end, wherein the first end is connected to the limiting portion, and wherein the retracted portion has a minimum diameter, the limiting portion has a first maximum diameter, and the first maximum diameter is greater than the minimum diameter; and
    an opening portion connected to the second end of the retracted portion, wherein the opening portion has a second maximum diameter, and the second maximum diameter is greater than the minimum diameter.

12. The implant of claim 11, wherein the limiting portion has a disc-shaped structure.

13. The implant of claim 11, wherein the opening portion comprises an against unit, and the against unit is disposed around an outer surface of the retracted portion and extends to an outer surface of the opening portion, and
    wherein the against unit comprises a connecting rod portion and a limiting against portion integrally formed with the connecting rod portion.

14. The implant of claim 13, wherein:
    the connecting rod portion is in contact with the outer surface of the opening portion; or
    the limiting against portion and the outer surface of the retracted portion are spaced apart from each other.

15. The implant of claim 14, wherein the retracted portion further comprises:
    a third solid structure adjacent to the limiting portion; and
    a fourth solid structure adjacent to the limiting against portion, wherein a diameter of the fourth solid structure is greater than the minimum diameter of the retracted portion.

16. The implant of claim 15, wherein the limiting against portion is against a surface of the fourth solid structure.

17. The implant of claim 11, wherein the opening portion comprises at least two arms, and the at least two arms are laterally collapsed or expanded relative to a central axis of the opening portion.

18. The implant of claim 17, wherein the at least two arms are equidistantly or non-equidistantly disposed around an outer periphery of the opening portion of the filling portion.

* * * * *